(12) United States Patent
Kreber et al.

(10) Patent No.: US 10,926,014 B2
(45) Date of Patent: Feb. 23, 2021

(54) CASSETTE MODULE

(71) Applicant: Fresenius Medical Care Deutschland GmbH, Bad Homburg (DE)

(72) Inventors: Stefan Kreber, Saarbruecken (DE); Manfred Weis, St. Wendel (DE); Marina Wenke, St. Wendel (DE); Lothar Leick, Merzig (DE)

(73) Assignee: FRESENIUS MEDICAL CARE DEUTSCHLAND GMBH, Bad Homburg (DE)

( * ) Notice: Subject to any disclaimer, the term of this patent is extended or adjusted under 35 U.S.C. 154(b) by 210 days.

(21) Appl. No.: 14/910,757

(22) PCT Filed: Aug. 6, 2014

(86) PCT No.: PCT/EP2014/002162
§ 371 (c)(1),
(2) Date: Feb. 8, 2016

(87) PCT Pub. No.: WO2015/018519
PCT Pub. Date: Feb. 12, 2015

(65) Prior Publication Data
US 2016/0184501 A1    Jun. 30, 2016

(30) Foreign Application Priority Data
Aug. 9, 2013 (DE) ...................... 10 2013 013 415.3

(51) Int. Cl.
*A61M 1/16* (2006.01)
*A61M 1/14* (2006.01)
(Continued)

(52) U.S. Cl.
CPC ............. *A61M 1/1601* (2014.02); *A61M 1/14* (2013.01); *A61M 1/34* (2013.01); *A61M 1/3403* (2014.02);
(Continued)

(58) Field of Classification Search
CPC ........ A61M 1/1601; A61M 1/14; A61M 1/34; A61M 1/3403; A61M 5/165;
(Continued)

(56) References Cited

U.S. PATENT DOCUMENTS 5,350,357 A    9/1994  Kamen et al.
2007/0278155 A1* 12/2007  Lo ........................... A61M 1/16
                                                              210/646

(Continued)

FOREIGN PATENT DOCUMENTS

DE       10335446      2/2005
WO    WO 84/02473      7/1984
(Continued)

*Primary Examiner* — Bobby Ramdhanie
*Assistant Examiner* — Donovan Bui-Huynh
(74) *Attorney, Agent, or Firm* — Jacobson Holman, PLLC

(57) ABSTRACT

The present invention relates to a cassette module for controlling fluid flows, in particular for use in blood treatment systems or in infusion systems, wherein the cassette module comprises at least one base body having means for the flow guidance of at least one fluid flow and at least two membranes which are at least sectionally directly or indirectly in contact with the base body, wherein at least one actuation element is arranged between the membranes by means of which the means for the flow guidance can be acted on.

4 Claims, 2 Drawing Sheets

Figure 1:
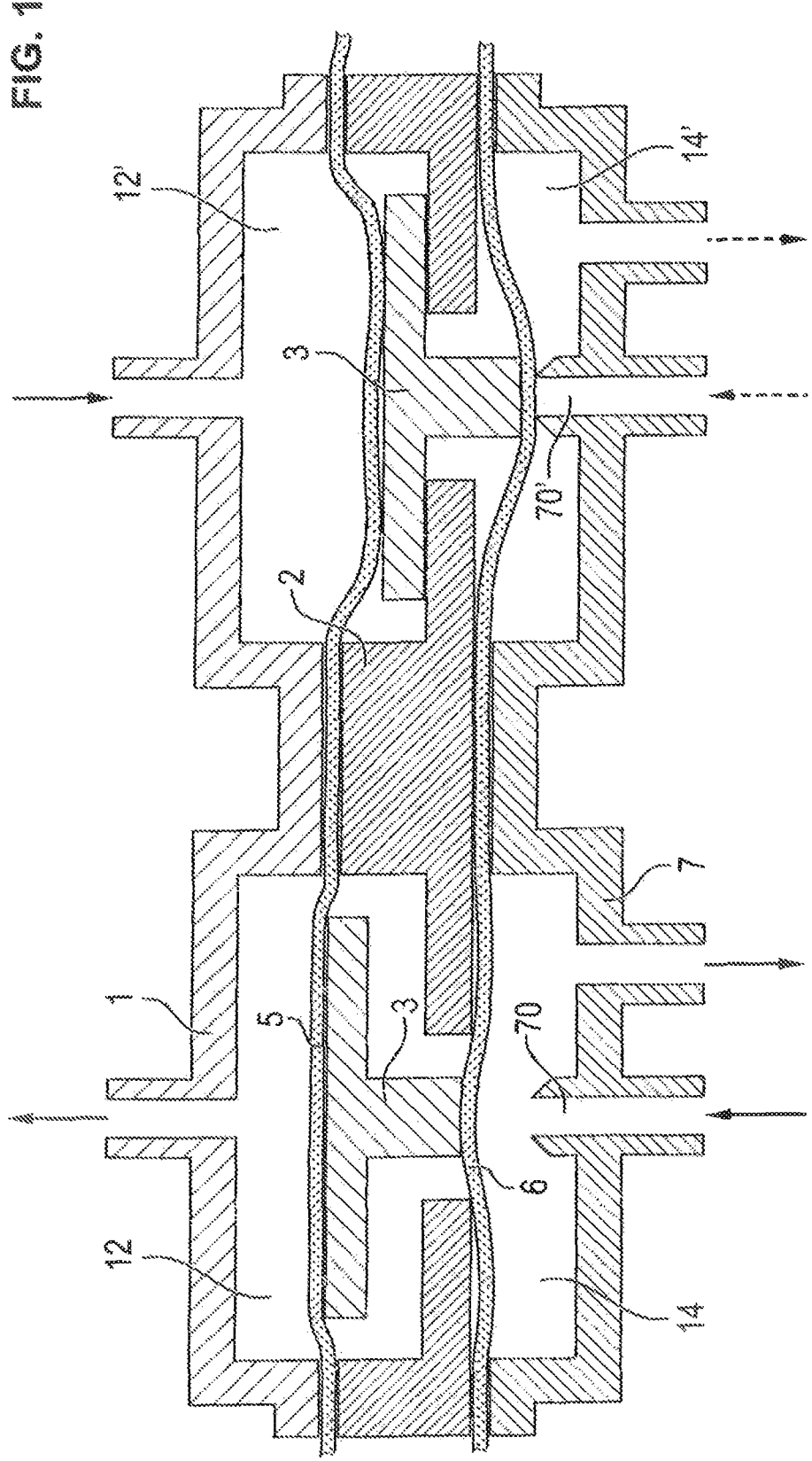

(51) Int. Cl.
  *B29C 65/16* (2006.01)
  *A61M 5/165* (2006.01)
  *A61M 1/26* (2006.01)
  *A61M 1/34* (2006.01)
  *B29C 65/00* (2006.01)
  *B23K 26/18* (2006.01)
  *B23K 26/244* (2014.01)
  *B29L 31/00* (2006.01)

(52) U.S. Cl.
  CPC ............ *A61M 5/165* (2013.01); *B23K 26/18* (2013.01); *B23K 26/244* (2015.10); *B29C 65/16* (2013.01); *B29C 65/1635* (2013.01); *B29C 65/1683* (2013.01); *B29C 66/1122* (2013.01); *B29C 66/5346* (2013.01); *B29C 66/543* (2013.01); *B29C 66/723* (2013.01); *B29C 66/727* (2013.01); *A61M 2005/1657* (2013.01); *A61M 2205/12* (2013.01); *A61M 2205/126* (2013.01); *A61M 2205/15* (2013.01); *A61M 2205/3331* (2013.01); *A61M 2207/00* (2013.01); *B29C 65/1616* (2013.01); *B29C 66/72341* (2013.01); *B29C 66/72343* (2013.01); *B29L 2031/753* (2013.01)

(58) Field of Classification Search
  CPC ...... A61M 2005/1657; A61M 2205/12; A61M 2205/126; A61M 2205/15; A61M 2205/3331; A61M 16/0616; A61M 16/207; A61M 1/1623; A61M 1/1652; A61M 1/1672; A61M 1/304; A61M 1/30; A61M 2205/1657; B23K 26/18; B23K 26/244; B29C 65/16; B29C 65/1635; B29C 65/1683; B29C 66/1122; B29C 66/5346; B29C 66/543; B29C 66/727; B29L 2031/753

See application file for complete search history.

(56) References Cited

U.S. PATENT DOCUMENTS

| 2009/0137940 | A1* | 5/2009 | Orr ..................... A61M 1/106 604/6.11 |
| 2010/0274168 | A1 | 10/2010 | Gronau |
| 2011/0028902 | A1 | 2/2011 | Siefert |
| 2011/0200791 | A1 | 8/2011 | Kugelmann |
| 2012/0167673 | A1 | 7/2012 | Farjam et al. |

FOREIGN PATENT DOCUMENTS

| WO | WO 2008/106440 | 9/2008 |
| WO | WO 2012/087798 | 6/2012 |

* cited by examiner

CASSETTE MODULE

The present invention relates to a cassette module for controlling fluid flows, in particular for use in blood treatment systems or in infusion systems.

Cassette modules are known from the prior art, for example for use in dialyzers, in particular in hemodialysis or peritoneal dialysis. These cassette modules have the task of being able to control or convey liquid flows, in particular blood, dialyzate or other liquids relevant to treatment, with the aid of integrated functional units within the framework of the treatment. Such functional units are, for example, valves, pumps, channels, etc. The flows of blood, dialyzate and other liquids relevant to treatment can be controlled by them.

Cassette modules can be manufactured in mass production due to the comparatively inexpensive plastics used and are frequently used as disposable articles.

The named valve functions and pump functions are known in cassette modules from the prior art. Flow channels and/or openings can be formed in cassette bodies which can be brought into contact with a movable membrane in order to be able to provide the named function in this manner. It is thus conceivable, for example, to use the membrane for pumping a liquid as well as to cover an opening etc. by the membrane in dependence on its position and thus to provide a valve function.

The deflection of the membrane itself can take place by a pneumatic actuation, for example.

A cassette module is known from EP 0 129 554 B1 which comprises two plates between which a movable membrane is arranged. This is controlled by a pneumatic actuation. For this purpose, one of the plates of the cassette module is designed as an actuator plate which is designed with channels and chambers in which excess pressure or underpressure can be generated as required.

U.S. Pat. No. 5,350,357 discloses a cassette module which can be operated via a pneumatic actuator module at the machine side. The cassette module comprises a base body which is covered by a membrane at its front side and rear side. The pneumatic control and thus the control of the liquid flows within the cassette module takes place via the pneumatic deflection of one of the membranes.

WO 2008/108440 A1 finally discloses a cassette which comprises three plates, wherein the liquid paths within the cassette module are substantially arranged on the center plate which is arranged between the two outwardly disposed plates. The required pump functions and valve functions can be generated via individual membranes. The deflection of the membranes takes place via pneumatic connections which are arranged in one of the plates.

In the cassette modules known from the prior art, the liquid to be conveyed is separated from the drive side, i.e. from the pneumatic side, by the named membrane.

The deflection of the membranes takes place via pneumatic connections which are arranged in one of the plates.

It is the underlying object of the present invention to further develop a cassette module such that a particularly reliable actuation of the means for the flow guidance of the fluid takes place.

This object is satisfied by a cassette module having the features of claim 1.

Provision is accordingly made that at least one actuation element is arranged between the membranes by means of which an influence can be effected directly or indirectly onto the means for the flow guidance.

If the means for the flow guidance are, for example, an opening or a valve, a pressure can e.g. be particularly reliably exerted on this opening, and thus the valve can be closed, by the named actuation element which is located between the two membranes.

The control or actuation of one or both membranes can take place, for example, pneumatically or also by a liquid, that is hydraulically.

A reliable force transmission from one membrane to the other membrane takes place by means of the named actuation element which can be designed, for example, as a plunger disk, plate, etc., which transmits the pressure which is exerted onto a membrane, e.g. pneumatically, preferably areally onto the second membrane. A particularly reliable closing of a channel, of an opening, etc. can, for example, thereby be effected.

The advantage furthermore results from the presence of two membranes that the tearing of one membrane does not result in an immediate contamination of the treatment liquid flowing in the cassette or of any other fluid by the actuator medium such as compressed air or a hydraulic medium. A discharge of the conveyed liquid or of the conveyed gas can correspondingly be prevented by two membranes.

The function exerted by the membrane, for example a valve function, can be exerted faster and more precisely due to the plunger disk disposed between the two membranes or other actuation element, which permits higher clock times of the valve switching procedures.

The invention furthermore relates to a cassette module for controlling fluid flows, in particular for use in blood treatment systems or in infusion treatments, wherein the cassette module comprises at least one base body having means for the flow guidance of at least one fluid flow and at least one membrane which is at least sectionally in connection directly or indirectly with the base body, wherein the membrane has a single-layer structure whose layer consists of or comprises a material absorbing laser light or has a multilayer structure which has at least one layer transmitting the laser light and at least one (preferably outer) layer absorbing the laser light, wherein the outer layer absorbing the laser light forms the connection region of the membrane to at least one further component of the cassette module.

It is conceivable that the membrane has two outer, laser light absorbing layers for bonding to two functional layers. The use of a monolayer membrane having a laser absorber for bonding to one or two functional layers is also possible and is also covered by the invention.

A laser light absorbing layer is understood as a layer which has a greater absorption for the laser light than the layer transmitting the laser light. Conversely, the layer transmitting the laser light has a smaller absorption for the laser light than the layer absorbing the laser light. The terms "absorbing layer" and "transmitting layer" are thus not necessarily to be understood such that the absorbing layer has a degree of absorption of 100% and the transmitting layer has a degree of absorption of 0%, although such a configuration is covered by the invention. The terms in particular illustrate a different absorption behavior of the layers and thus also a different heating on being acted on by laser light. The values of 100% and 0% degree of absorption are limit values which are only possible in accordance with physical law. Generally a minimal absorption will be able to be observed in the transparent part of the layer and a specific transmission in the opaque part of the layer.

A reliable connection between the membrane and at least one further component of the cassette module, for example the base body, is achieved in that thus at least one multilayer membrane is used. The layer absorbing the laser light is heated by the application of laser light so that a "welding" of the membrane to at least one further part of the cassette module takes place. The layer transmitting the laser light is in contrast not heated or is hardly heated or less heated and in particular serves the ensuring of the mechanical stability of the membrane.

Since an underpressure can also be present on the fluid side, i.e. on the side of the fluid whose flow is to be controlled, it is necessary to couple the actuator side and the fluid side of the valve or of the other cassette body to one another since otherwise, with a closed valve and an applied underpressure to the fluid side, the passage could no longer be opened by applying an underpressure. This problem can be remedied if the two membranes are welded to one another on their adjacent sides.

The terms "underpressure" and "excess pressure" are not only to be understood as values relative to atmospheric pressure, but also as values relative to one another. This means, for example, that "underpressure" does not necessarily have to mean vacuum, although this is possible.

The process of transmission welding by means of a laser brings along the advantage that the film can also still be heated when it is already arranged between two parts to be connected, i.e. is no longer directly accessible from the outside.

In a further embodiment of the invention, the two above-named ideas can be present in combination. This means that the cassette module can be configured with the features of claim 1 as well as also with the features of claim 2.

The further component to which the membrane is connected can, for example, be the base body or a part of the base body of the cassette module or also a further membrane or also the above-named actuation element such as the plunger plate.

Provision can furthermore be made that the membrane has an at least three-layered design, with at least two layers absorbing the laser light (preferably as outwardly disposed layers) and at least one layer arranged therebetween and transmitting the laser light being present.

Provision can furthermore be made that the cassette module has at feast one functional layer and at least one second functional layer, with the first functional layer having means for the flow guidance of at least one fluid flow, in particular of at least one liquid flow, and wherein the second functional layer is arranged between the two membranes.

Provision is made in a further embodiment of the invention that the cassette module has a third functional layer which has means for actuating one or both membranes.

The third functional layer can have chambers, channels or the like, for example, via which at least one of the membranes can be deflected via a pneumatic or hydraulic actuation.

The means for actuating at least one of the membranes are preferably pneumatic means, in particular chambers or channels, in which excess pressure or underpressure is present or can be generated.

Provision is made in a further embodiment of the invention that the means for the flow guidance of a fluid flow such as of a liquid flow or a gas flow have one or more channels, valves and pump sections.

Provision can further be made that the named functional layers comprise a flexurally stiff material, preferably plastic. The named membrane is flexible and preferably elastic.

It is not absolutely necessary in the sense of the Invention that the membrane is arranged areally between the functional layers, although such an embodiment is likewise covered. The membrane can also be arranged sectionally limited to respective actuation elements of the functional layers.

The cassette module is preferably designed as a disposable article.

The present invention furthermore relates to a machine, in particular to a blood treatment machine or to an infusion machine, such as a hemodialysis machine or a peritoneal dialysis machine, having at least one slot in which at least one cassette module in accordance with one of the claims 1 to 11 is located.

The present invention furthermore relates to a method of manufacturing a cassette module in accordance with one of the claims 1 to 11, wherein the connection of the membrane to at least one further component of the cassette module takes place by means of transmission welding using a laser, wherein the heating of the at least one layer of the membrane absorbing the laser light takes place.

Provision is preferably made in this respect that the membrane is located in its state inserted into the base body when the transmission welding is carried out. To make this possible, the material of the base body is permeable for the laser light in this case.

Figure 2:
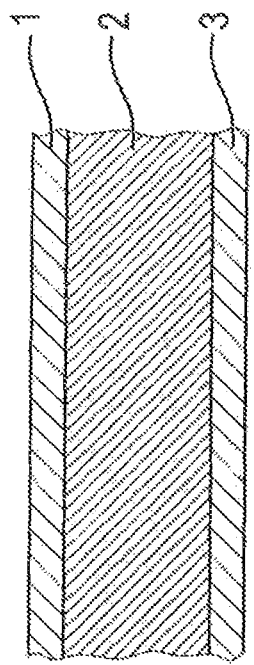
Figure 3:
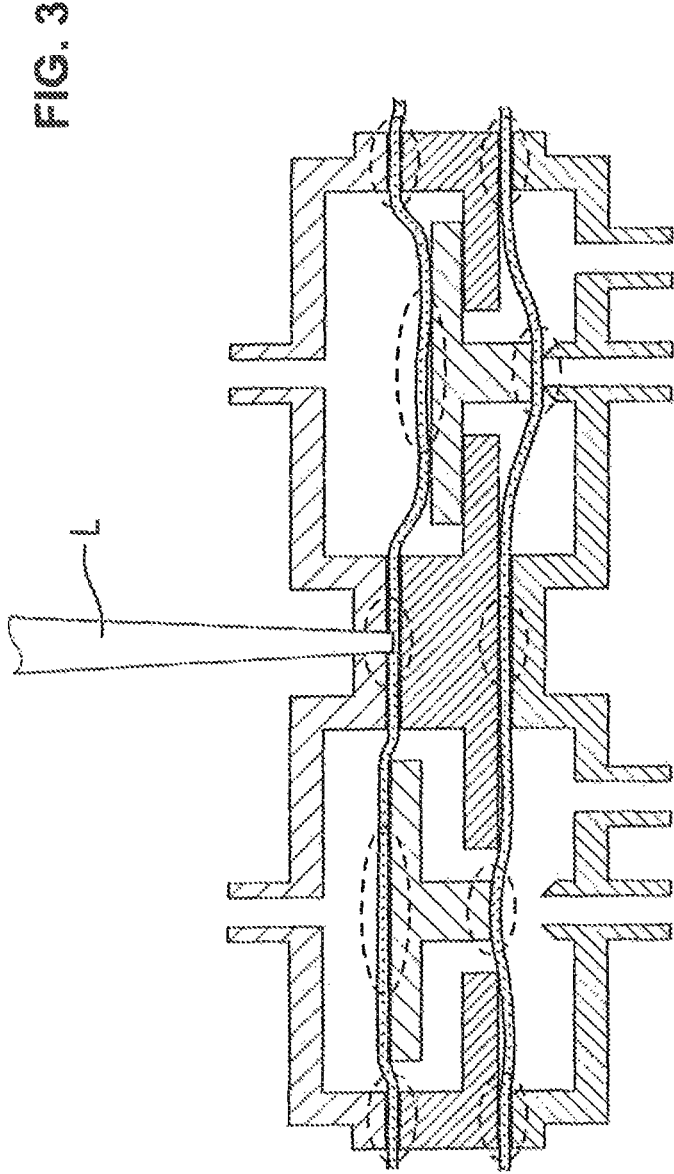

Further details and advantages of the invention will be explained in more detail with reference to an embodiment shown in the drawing. There are shown:

FIG. 1: a sectional view through a cassette module in accordance with the present invention;

FIG. 2: a sectional view through a membrane such as can be used in the cassette module in accordance with the invention; and FIG. 3: a further sectional view through a cassette module in accordance with the invention.

FIG. 1 shows a longitudinal sectional view through a cassette module in accordance with the invention.

The first functional layer is marked by the reference numeral 7 and the second functional layer is marked by the reference numeral 2.

Reference numeral 1 marks the third functional layer.

As can be seen from the Figure, the second functional layer 2 is located between the first functional layer 7 and the third functional layer 1.

Furthermore, a first membrane 6 is located between the second functional layer 2 and the first functional layer 7 and a second membrane 5 is located between the third functional layer 1 and the second functional layer 2.

As can furthermore be seen from the Figure, a respective one plunger or a respective one plunger plate 3 is located between the membranes 5, 6 in both chambers shown which equally serves as a valve for closing or releasing an opening 70, 70' in the first functional layer 7.

As can further be seen from the Figure, means for the flow guidance of at least one liquid flow such as blood, dialyzate, an infusion solution, etc. are located in the first functional layer 7, wherein in the embodiment shown here, the means are configured in the form of a valve which allows or prevents a throughflow of the chambers 14, 14' of the cassette module.

As can further be seen from the Figure, the valve block or the cassette module designed as a valve block has two such valves, wherein the valve having the opening 70 in the chamber 14 of the cassette module shown at the left being open and the valve having the opening 70' in the chamber 14' of the cassette module shown at the right being closed.

The opening of the valve takes place in that underpressure is generated in the pneumatic chamber 12 as shown by an arrow. This has the result that the second membrane 5 and, due to the vacuum present between the membranes, also the first membrane 6 as well as also the plunger plate 3 are moved upwardly, whereby the opening 70 is released by the membrane 6. A fluid flow through the fluid chamber 14 is thereby made possible.

In the chamber 12' of the cassette module shown at the left, in contrast, an excess pressure is generated, as is symbolized by the arrow shown which symbolizes the inflow of a pneumatic fluid, in particular of compressed air. The two membranes 5, 6 as well as also the plunger plate 3 shown at the right are thereby urged downwardly and the opening 70' is closed by means of the first membrane 6. The chamber 14' can thus not be flowed through by a fluid, as is indicated by the dashed arrows.

As already stated above, the terms excess pressure and underpressure do not necessarily mean that an excess pressure or underpressure relative to atmospheric pressure has to be present, although such an embodiment is also covered. They can also mean values relative to one another.

It is thus conceivable, for example, that an underpressure in the chamber 12 does not only mean that vacuum is applied by a pump in the chamber 12. It can also mean that a liquid is flowed into the chamber 14 by the operation of the cassette without, however, actuation taking place in the chamber 12. The membranes 5, 6 are then deflected and the chamber 12 represents the underpressure side with respect to the chamber 14 without a vacuum being actively applied in the chamber 12.

It is conceivable that the pressure in the functional layer 2 is smaller than in the layers 1 and 14.

The cassette module shown in the Figure is a valve block. Any desired other functionalities are generally also covered by the invention such as a pump function or the like.

The functional layers 1, 2, 7 comprise a flexurally stiff plastic, i.e. a stable-shape plastic, whereas the membranes 5, 6 are designed as flexible, preferably elastic membranes so that the desired flow guidance can be set.

It can further be seen from the Figure that both the first functional layer 7 and the third functional layer 1 have flared portions which form chambers 12, 14, 12', 14' which serve, on the one hand, for controlling the membranes via an actuator medium such as compressed air and, on the other hand, for controlling a fluid flow such as blood, dialyzate, infusate, etc.

The cassette module shown is naturally not only suitable for controlling a liquid flow, but also, for example, to control a gas flow.

The control via the chambers 12, 12' also does not necessarily have to take place using a gas or compressed air, but can rather likewise take place via a fluid, i.e. hydraulically.

The valve shown or the plunger plate 3 is brought into the one or other end position by the excess pressure or underpressure in the chambers 12, 12' and closes or opens a fluid circuit or the opening 70, 70' with its side opposite the pneumatic system or hydraulic system in dependence on its instantaneous position.

The end positions can, for example, be formed by surfaces or functional layers such as by the second functional layer. In the right chamber, the plate-shaped region of the plunger plate abuts the second functional layer so that an end position is thereby defined.

The control circuit, for example the pneumatic circuit, and the fluid circuit, for example a circuit for conveying blood, dialyzate, etc., are reliably separated by the presence of two membranes 5, 6 so that no contamination can occur on the tearing of a membrane.

The membrane 5 is preferably in direct contact with the functional layers 1 and 2 and the membrane is preferably in direct contact with the functional layers 2 and 7.

It is pointed out at this point that the term "membrane" is to be understood widely and covers any areal and movable material which can carry out the named functions. The membranes can, for example, be configured as films.

They are preferably impermeable for the fluid as well as also for the actuator medium (such as compressed air, hydraulic medium, etc.). They are furthermore largely impermeable for gas.

The movement or valve function exerted by the second membrane 5 takes place faster and more precisely due to the plunger disk 3 located between the membranes 5, 7. This allows higher clock rates of the valve switching, which is desirable.

A possible realization of the coupling between the pneumatic circuit and the fluid circuit comprises welding the two membranes 5, 6 to the respective sides adjacent to them. The involved housing parts, i.e. the named functional layers, also have to be connected to one another.

An inexpensive and also technically simple realization of this connection comprises that at least one or both of the membranes 5, 6 shown in FIG. 1 are partially heated and thus the adjacent hard components being welded to one another. The membranes thus serve as connection means for the functional layers.

The membrane can in this respect furthermore satisfy the valve function or sealing function required for the embodiment in accordance with FIG. 1.

To prevent an excessive heating for the purpose of welding the membrane, the membrane has at least one layer which transmits the laser light.

The wavelength of the laser can be selected such that the plastic material of the functional layers used is permeable for this light, whereas the layers 1 and 3 of the membrane shown in FIG. 2 have portions absorbing the laser light and are thus heated in the transmission.

An Nd:YAG laser is preferably used within the framework of the method in accordance with the invention.

Lumogen IR 788 BASF can, for example, be used as the absorber or absorbing material which absorbs in the infrared region so that the components provided therewith are largely transparent in the wavelength of visible light. The absorber is preferably admixed into the membrane material with a concentration of 100 ppm.

FIG. 2 shows an exemplary structure of this membrane 5, 6 and illustrates that the membrane has two cover layers 1, 3 which are designed as absorbing the laser light and has a middle layer 2 which is disposed therebetween and which has a smaller degree of absorption for the laser light and thus is not heated or is only heated slightly more than the layers 1, 3.

Due to the fact that the membrane only has thin layers 1, 3 of a laser light absorbing material at its outer sides, a high temperature is also only generated there, i.e. at contact points to the hard parts or components of the base body or functional layers to be welded, whereas the shown middle layer 2 is not heated or is only heated a little and the stability of the structure and the plastic and elastic properties of the membrane are largely maintained.

A welding can take place in the interior of the total structure due to the materials of the base body, i.e. in particular functional layers, transparent for the laser light used, i.e. a welding can take place after the at least one membrane has already been inserted.

FIG. 3 shows the weld points, marked by circled regions, at which the membrane is connected to at least one further component by the method in accordance with the invention. The laser beam is marked by the reference symbol L. The connection can be made to the plunger disk, to the base body or functional layer and/or to a further membrane.

Both individual weld spots can be set and thin tracks, e.g. for enclosing the areas to be sealed, can be drawn by the welding by means of a laser. The heat input and thus the load on the cassette module to be welded can be kept very small by the direct introduction of the welding energy only onto the required material amounts.

The invention claimed is:

1. A cassette module, wherein the cassette module comprises
    at least one base body having a first flow system including channels, chambers, valves, and pump sections for controlling at least one fluid flow,
    at least two membranes at least sectionally directly or indirectly in contact with the base body,
    at least one movable actuation plunger or plunger plate arranged between the two membranes, and capable of transferring force between the two membranes, by which the first flow system can be acted on,
    at least one first functional layer, at least one second functional layer, and a third functional layer, wherein the first functional layer has the first flow system, wherein the second functional layer is arranged between the two membranes, and wherein the third functional layer has a second flow system including the chambers and the channels for actuating one or both of the two membranes hydraulically or pneumatically, wherein the plunger has two end positions, at least one of the two end positions being formed by the second functional layer.

2. A cassette module in accordance with claim 1, characterized in that at least one of the functional layers comprises flexurally stiff material.

3. A cassette module in accordance with claim 1, characterized in that the two membranes are elastic membranes.

4. A machine, having at least one slot in which at least one cassette module in accordance with claim 1 is located.

* * * * *